United States Patent
Gravem et al.

(10) Patent No.: US 8,961,438 B2
(45) Date of Patent: Feb. 24, 2015

(54) SYSTEM FOR EVALUATING INFANT MOVEMENT

(75) Inventors: Dana Gravem, Laguna Beach, CA (US); Donald Patterson, Irvine, CA (US); Pai Chou, Irvine, CA (US); Daniel Cooper, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 286 days.

(21) Appl. No.: 13/218,528

(22) Filed: Aug. 26, 2011

(65) Prior Publication Data

US 2012/0059283 A1   Mar. 8, 2012

Related U.S. Application Data

(60) Provisional application No. 61/377,207, filed on Aug. 26, 2010.

(51) Int. Cl.
| | |
|---|---|
| *A61B 5/103* | (2006.01) |
| *A61B 5/11* | (2006.01) |
| *A61B 5/00* | (2006.01) |
| *A61B 5/16* | (2006.01) |

(52) U.S. Cl.
CPC ............ *A61B 5/1124* (2013.01); *A61B 5/7275* (2013.01); *A61B 5/168* (2013.01); *A61B 5/0002* (2013.01); *A61B 2503/045* (2013.01); *A61B 5/16* (2013.01); *A61B 5/1114* (2013.01); *A61B 2503/04* (2013.01)
USPC ........................................................ 600/595

(58) Field of Classification Search
USPC ........................................................ 600/595
See application file for complete search history.

(56) References Cited

PUBLICATIONS

Meinecke et al. "Movement analysis in the early detection of newborns at risk for developing spasticity due to infantile cerebral palsy" Journal of Human Movement Science, pp. 125-144. Feb. 3, 2006.*
Heinze et al. "Movement Analysis by Accelerometry of Newborns for the Early Detection of Movement Disorders due to Infantile Cerebral Palsy" IFMBE Proceedings vol. 25/9, 2009, p. 24-27.*
Park "Eco: Ultra-wearable and Expandable Wireless Sensor Platform" Apr. 2005 (as submitted by applicant).*
Heinze and Hesels et al. "Movement analysis by accelerometry of newborns nad infants for the early detection of movement disorders due to infantile cerebral palsy" Med Biol Eng Comput (2010) 48; 765-772.*
Mingming Fan, Dana Gravem, Dan Cooper, Donald J. Patterson, "Augmenting Gesture Recognition with Erlang-Cox Models to Identify Neurological Disorders in Premature Babies," Proceedings of the 2012 ACM Conference on Ubiquitous Computing, 2012, pp. 411-420.
D. Gravem, M. Singh, C. Chen, J. Rich, J. Vaughan, K. Goldberg, F. Waffarn, P. Chou, D. Cooper, D. Reinkensmeyer, and D. Patterson, "Assessment of Infant Movement With a Compact Wireless Accelerometer System," J. Med. Devices 6, 021013 (2012).
Singh, M. and Patterson, D., "Involuntary Gesture Recognition for Predicting Cerebral Palsy in High-Risk Infants," Proc. ISWC, 2010, pp. 1-8.

(Continued)

*Primary Examiner* — Max Hindenburg
*Assistant Examiner* — Renee Danega
(74) *Attorney, Agent, or Firm* — Michael Fedrick; Loza & Loza, LLP

(57) ABSTRACT

A system and method for measuring movements, utilizing one or more wireless accelerometers attached to one or more limbs of a human subject for the purpose of determining certain temporal and spatial gestures of the subject.

15 Claims, 13 Drawing Sheets

(56) References Cited

PUBLICATIONS

Hayes, G.R., Patterson, D.J., Singh, M., Gravem, D., Rich, J., and Cooper, D., "Supporting the Transition from Hospital to Home for Premature Infants Using Integrated Mobile Computing and Sensor Support," Personal and Ubiquitous Computing, 2011, (15)8: 871-885.

Heinze, F., Hesels, K. Breitbach-Faller, N., Schmitz-Rode, T. and Disselhorst-Klug, C., "Movement analysis by accelerometry of newborns and infants for the early detection of movement disorders due to infantile cerebral palsy," Med Biol Eng Comput (2010) 48:765-772.

Park, C., Chou, P., and Sun, Y., "A Wearable Wireless Sensor Platform for Interactive Dance Performances," Fourth Annual IEEE International Conference on Pervasive Computing and Communications, Mar. 13-17, 2006, pp. 53-59.

Chulsung Park, Jinfeng Liu, and Pai H. Chou, "Eco: An Ultra-Compact Low-Power Wireless Sensor Node for Real-Time Motion Monitoring," Proceedings of the Fourth International Symposium on Information Processing in Sensor Networks, Apr. 25-27, 2005, pp. 398-403.

Chulsung Park and Pai H. Chou, "Eco: Ultra-Wearable and Expandable Wireless Sensor Platform," 2006 International Workshop on Wearable and Implantable Body Sensor Networks (BSN 2006), Apr. 3-5, 2006, pp. 162-165.

Tsai, Yi-Lung, Tu, Ting-Ting, Bae, Hyeoungho, Chou, Pai H. "EcoIMU: A Dual Triaxial-Accelerometer Inertial Measurement Unit for Wearable Applications," 2010 International Conference on Body Sensor Networks (BSN), Jun. 7-9, 2010, pp. 207-212.

\* cited by examiner

Figure 8

| ID# | GA at birth | Birth Wt | GA at monitoring |
|---|---|---|---|
| ID 1 | 28 | 1480 | 30 |
| ID 2 | 25 | 860 | 36 |
| ID 3 | 36 | 2150 | 37 |
| ID 4 | 24 | 880 | 34 |
| ID 5 | 26 | 765 | 36 |
| ID 6 | 25 | 690 | 43 |
| ID 7 | 26 | 800 | 35 |
| ID 8 | 25 | 680 | 39 |
| ID 9 | 28 | 1150 | 36 |
| ID 10 | 28 | 1180 | 37 |
| AVERAGE | 27.1 wk | 1063.5 gm | 36.3 wk |

Figure 9

| Function | mean, maximum, minimum, standard deviation, z-value |
|---|---|
| Window Length | 1 sec, 2 sec, 4sec |
| Data | $f^{left-arm}, f^{right-arm}, f^{left-leg}, f^{right-leg}, f^5, f^6, f^7, f^8, f^9$ |
| | $f^{10}$ |

Figure 10

| Baby ID | Sensitivity (Random Forest) | Sensitivity (SVM) | Specificity (Random Forest) | Specificity (SVM) | Cramped Synchronous Movements |
|---|---|---|---|---|---|
| 1 | N/A | N/A | 0.99985643 | 0.999971087 | No |
| 2 | 0.993799823 | 0.947012401 | 0.999747291 | 0.964881833 | Yes |
| 3 | N/A | N/A | 0.9999355 | 0.999870997 | No |
| 4 | 0.994413408 | 0.981270358 | 0.999737517 | 0.979102519 | Yes |
| 5 | 0.992682034 | 0.979439252 | 0.99983395 | 0.985316732 | Yes |
| 6 | 0.9940197 | 0.970336566 | 0.999574475 | 0.957825254 | Yes |
| 7 | 0.994724221 | 0.986206897 | 0.999970463 | 0.990684744 | Yes |
| 8 | 0.985053381 | 0.963210702 | 0.99990804 | 0.99013058 | Yes |
| 9 | N/A | N/A | 0.99990056 | 0.998963024 | No |
| 10 | N/A | N/A | 0.99998908 | 0.983752145 | No |
| Average | 0.992448761 | 0.97124603 | 0.99984523 | 0.98504989 | |

SYSTEM FOR EVALUATING INFANT MOVEMENT

CROSS REFERENCE TO RELATED APPLICATIONS

This application claims the benefit of priority from U.S. Patent Application No. 61/377,207, filed on Aug. 26, 2010 and entitled DEVICE TO MEASURE MOVEMENT & METHODS OF USE THEREOF, the disclosure of which, including its drawings, is incorporated herein by reference in its entirety.

GOVERNMENT LICENSE RIGHTS

This invention was made with Government support under Grant No. NR009070, awarded by the National Institutes of Health. The Government has certain rights in this invention.

BACKGROUND OF THE INVENTION

Over the past two decades, the incidence of preterm births has increased dramatically. Technological advances in the medical and health sciences have increased the survivability of these preterm infants. The increase in survival, however, has been accompanied by an increase in the incidence of long-term complications associated with premature births such as cerebral palsy (CP), with approximately 10% of preterm infants developing CP. Early diagnosis of CP and other motor abnormalities may enable clinicians to implement early interventions and provide an improved quality of life. Diagnosis is usually made between several months and 2 years of age.

Attempts have been made to develop techniques to be able to detect movement patterns predictive of neurological dysfunction such as CP. One conventional tool for diagnosis of CP is the physician's neurological exam. This exam focuses on the infant's reflexes but places little importance on spontaneous movements. It has been found however that spontaneous movements have a higher predictive value for the development of cerebral palsy compared to reflexive movements. As a result, early diagnosis of CP is often unreliable.

Another tool for diagnosis of CP is the so-called General Movements Assessment (GMA), a technique focused on an infant's spontaneous movements. The GMA is an observational assessment that judges the quality of infant movements and identifies key movements which are markers of neurological dysfunction. General Movements (GMs) of the infant are defined as movements involving the entire body of the infant. Specifically, GMs are a distinct movement pattern carried out spontaneously without external stimulation and seen in fetuses of nine (9) weeks gestational age until about twenty-one (21) weeks post-term. In normal infants, these movements are elegant, smooth and variable in sequence, intensity and speed with a clear beginning and end. The GMA identifies cramped synchronized general movements as one type of abnormal movement. These movements are rigid in nature with the infant's limbs moving in synchrony. The presence of cramped synchronized movements has been shown to have a high predictive value for the development of cerebral palsy.

These conventional approaches to analyze infant movement involve directly observing or videotaping subjects for variable periods of time and then qualitatively analyzing their movements using validated movement scales. One problem with video/direct observation is observer fatigue. One study focusing on natural patterns of physical activity in 6-8 year old children indicated that with a 3-second observation protocol, a typical observer needs a substantial break after about 20 minutes. Moreover, attempting to quantify activity of four (4) limbs in a preterm infant by direct observation is a challenging task, even for the most adept observer. In addition, the clinician must have extensive training in order to accurately carry out these techniques. The time commitment for appropriate training is not always feasible for the neonatal physician or occupational therapist.

SUMMARY

In one embodiment, the present invention comprises a system for determining an infant's risk for experiencing a medical disorder, such as a neurological or motor skills disorder. The system comprises one or more wireless accelerometers for attachment to one or more extremities of an infant subject, with each accelerometer configured to measure physical movement from one of the subject's extremities, such as an arm and/or a leg. The wireless accelerometers preferably weigh less than 5 grams and have a surface area of 1 $cm^2$ or less in order to facilitate their use with infants. The system further comprises a base station in wireless communication with the accelerometers and a processing circuit electrically coupled to the base station. The processing circuit, which can be in a computer or server, is adapted to perform statistical analyses of data from the accelerometers and to compare the processed data to a reference standard in order to determine whether the subject is at risk of experiencing the medical disorder. The processing circuit can utilize a statistical machine learning technique such as Naïve Bayes, Support Vector Machines, and a pruned Decision Tree. The medical condition being diagnosed can be, for example, cerebral palsy, mental retardation, autism and/or intraventricular hemorrhage.

In another embodiment, the present invention comprises a method for diagnosing whether an infant subject is at risk for a predetermined medical condition such as cerebral palsy, mental retardation, autism or intraventricular hemorrhage. The method is particularly useful for diagnosing infants born prematurely. The method involves measuring the movements of a plurality of the subject's limbs, wherein the measuring is performed by a plurality of wireless accelerometers attached to the plurality of limbs. The plurality of accelerometers provides data wirelessly to a base station, which either then processes the data or transfers it to a device with a processor capable of performing such data processing, including normalizing the data. One or more features is then calculated using the normalized data, and the features are compared to a reference standard to determine whether the subject demonstrates certain predetermined movements which indicate that the subject is at risk for a medical condition. The presence of the predetermined movements, such as Cramped-Synchronized General Movements, indicates that the subject may be at risk for a neurological or motor skills impairment.

DRAWINGS

FIG. 8 is a table of the gestational age (GA) of test subjects.

FIG. 9 is a table of temporal feature calculation components.

FIG. 10 is a table of modeling results.

DETAILED DESCRIPTION

Definitions

Figure 1:
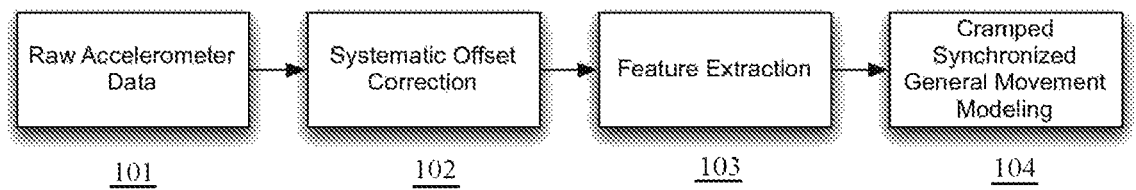
FIG. 1 is a flow chart illustrating the processing of data from an accelerometer to a base station according to an embodiment of the present invention.

As used herein, the following terms and variations thereof have the meanings given below, unless a different meaning is clearly intended by the context in which such term is used.

"Accelerometer" refers to a device or component that measures acceleration.

"Adapted to," in regard to a processing circuit, refers to the processing circuit being configured, employed, implemented, or programmed, as well as any combination thereof, to carry out a process, function, step or routine.

"Base station" refers to an electronic component of the present comprising a receiver or transceiver and circuitry adapted to receive data from the wireless accelerometers of the present system. The base station may also comprise circuitry for processing and/or further transmitting such data as described herein. The base station may be a separate electronic component or may be a computer system with appropriate hardware or software for receiving and processing data from the wireless accelerometers.

"Computer system" refers to any electronic data processing device adapted to execute software instructions. By way of example and not limitation, a computer system can include a desktop computer, a laptop computer, a notebook computer, a tablet (e.g., iPAD®), a personal media player (e.g., iPOD®, ZUNE®), a smart phone (e.g., iPHONE®, DROID®, BLACKBERRY®), or other data processing device.

"Extremity" refers to a hand, foot, or limb (arm or leg) of a subject, preferably a human infant.

"Infant" refers to a subject who is less than 2 years of age, preferably less than 1 year old, and more preferably less than 6 months old, although being at least newborn.

"Premature infant" refers to an infant born prior to the end of a normal gestational term.

"Software program" refers to a collection of processor executable code or code segments that provide instructions telling a processor what to do. As used herein, the term "software programs" can include software, firmware, middleware, testware or microcode as well as any combination thereof.

"Wireless accelerometer" refers to an electronic component of the present system comprising an accelerometer and a transmitter for wirelessly transmitting data gathered by the accelerometer.

The term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise.

System

The present system measures, quantifies and analyzes spontaneous movements of infants in order to predict the likelihood that an infant may suffer from a neurological disorder. The system preferably includes one or more wireless accelerometers adapted to be reversibly attached to one or more extremities (limbs, hands, or feet) of an infant, at least one base station in wireless communication with the accelerometers, and software running on the base station or on another device which analyzes the resultant signals from the accelerometers. The wireless accelerometers detect and measure physical movement of the infant, and this data is transmitted to the base station which records the data during a predetermined monitoring time period.

Generally, an accelerometer measures changes in velocity over time ($m/s^2$). The accelerometer of the present system preferably weighs 2 grams or less and is capable of measuring acceleration along three axes (x, y, and z axes). It also preferably has a small surface area, for example an area of 12 mm×12 mm square. The accelerometer may be more or less than 2 grams, but should be light enough so that it does not interfere with spontaneous movements of an infant when placed on the infant's limbs.

Each accelerometer preferably takes measurements between 10 and 100 times per second. When more than one accelerometer is used with the present system, the accelerometers are adapted to operate in a coordinated manner. Preferably, all such accelerometers are synchronized to the same clock and take samples at the same time. In addition, the accelerometers preferably communicate with the base station at different times so that they do not interfere with each other.

The accelerometers used in the present system are in electrical communication with a transmitter or transceiver so that acceleration data measured by the accelerometers can be transmitted wirelessly to a base station. The wireless accelerometers of the present system preferably weigh 5 grams or less, and are 1 $cm^2$ in surface area or less, in order to facilitate their use with an infant. The transmission of data by transmitters of the wireless accelerometer component can take place in real time, but in order to allow greater flexibility in the system the data is preferably transmitted with a predetermined latency or delay, such as a 3 second delay. The use of wireless communication allows the movement of an infant's extremities to be measured without the possibility of the infant's extremities becoming tangled with wires that would otherwise be used for a wired connection, thereby avoiding measurement errors and infant discomfort.

The wireless accelerometers of the present system can be attached to an extremity of an infant in any of a number of ways known to the art. Preferably, a wireless accelerometer to be attached to an infant is secured to strap which can be reversibly secured to the infant's extremity, such as with hook and loop fasteners. Other fasteners known to the art can also be used. In an alternative embodiment, the accelerometer can be attached to the infant using a medically acceptable adhesive.

The wireless accelerometers can be attached to one or more limbs of an infant, for example to the left arm (LA), right arm (RA), left leg (LG) and right leg (RG). In one embodiment, data from all four limbs of an infant is collected for diagnostic purposes. However, data can be collected from just one limb for diagnostic purposes as well. The accelerometers capture movements from the one or more limbs which ultimately correlate to type, number, synchronicity and frequency (among other information) of limb movement during a predetermined time period, i.e., a monitoring period.

The wireless accelerometers communicate acceleration data to a base station, which can comprise a receiver or transceiver for receiving the acceleration data and circuitry for communicating such received data. The base station can, in one embodiment, also comprise circuitry for processing such data as described herein. Alternatively, the base station can be a separate electronic component which transmits the data received from one or more wireless accelerometers to a computer or server with appropriate hardware and/or software for processing the data from the wireless accelerometers. The computer and/or server may be local or remote in this case preferably comprises software stored in memory for processing, interpreting and modeling the data, for example by comparing the processed data to standards to categorize an infant as being at high risk or low risk for development of a neurological disorder.

The base station receives data over the wireless link from one or more accelerometers, preferably one at a time. Depending on the total number of accelerometers, sampling rate, and latency, multiple base stations may need to be used. Each base station can define its own frequency hopping sequence to work with its set of accelerometers.

In one embodiment, dynamic switching between different channels can be used to receive the accelerometer data. This can in some cases limit the sampling rate of the entire system. Therefore, in a preferred embodiment, two or more base stations are used to gather data from a plurality of accelerometers simultaneously. In one embodiment utilizing four wireless accelerometers, a first base station's frequency can be set to 2.4 GHz, and it can then gather data from two accelerometers that transmit data at 2.4 GHz and 2.4 GHz+8 MHz. A second base station's frequency can be shifted to 2.45 GHz, so that it communicates with the other two accelerometers at 2.45 GHz and 2.45 GHz+8 MHz. Each base station then packages the data from the two accelerometers and forwards them to a host computer for processing.

Figure 2:
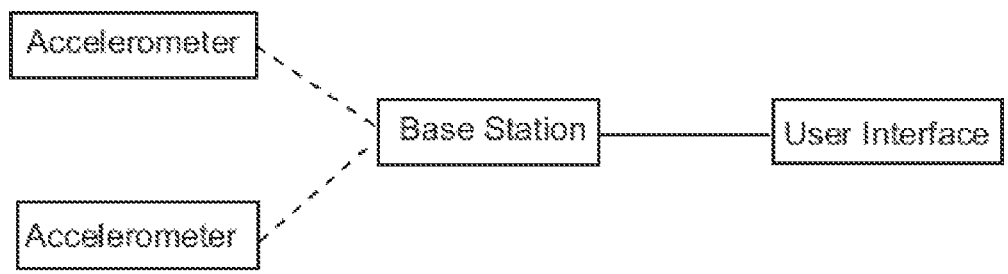
FIG. 2 is a block diagram of an embodiment of the present system.

A simplified diagram of an embodiment of the present system is shown in FIG. 2. As seen in that figure, one or more wireless accelerometers are placed in wireless communication with a base station (as indicated by the dotted lines). Data gathered by the accelerometers is then communicated (either through a wired, wireless, or networked connection) from the base station to a computer which processes the data. A user interface connected to the computer can be used to manipulate the raw or processed data, as well as to send instructions to the base station and/or wireless accelerometers.

Data Processing

FIG. 1 is a flow chart illustrating the processing of data from the accelerometer to the base station in one embodiment. Raw data is gathered by the base station from the one or more accelerometers attached to the extremities of a subject (101). The raw data is then cleaned and smoothed to eliminate missing data and accelerometer drift (102). The cleaned data is then pre-processed to extract features for analysis (103). The data is then statistically analyzed for clinical use (104).

Block 101 represents the raw accelerometer data captured from the one or more accelerometers. According to one embodiment, the raw accelerometer data consists of data points for three (3) different axes, i.e., the X, Y and Z axes wherein each axis consists of nineteen (19) points per second, i.e., a resolution of 19 Hertz (Hz).

Block 102 represents the cleaning and smoothing of the raw accelerometer data. Cleaning and smoothing of the data comprises calculating the mean for each axis, i.e., gravity due to change in position. The first step in the data pre-processing is to smooth the raw data by translation by standardizing the data points by centering on the mean, as shown in the equation below:

$$t'_{i,j} = t_{i,j} - \text{mean}(R_j) \; [i \in 1:N, j \in x,y,z]$$

$$R_x = (x_i - 90) + (x_i + 90)$$

$$R_y = (y_i - 90) + (y_i + 90)$$

$$R_z = (z_i - 90) + (z_i + 90) \hspace{2cm} \text{Equation 1A}$$

where j represents each axis (x, y, z), i represents an index for each data, and N represents the number of data points. This step is repeated for each of the individual axes and for every data point i in N. The length of R is not constant in Equation 1A as data is collected non-uniformly. That is, the size of sliding window for R changes and the mean is adjusted accordingly. The adjustment removes artifacts due to the constant forces of gravity and accelerometer calibration drift without reducing the number of data points. The smoothed values for individual x, y, z axes are then converted into a magnitude by the following equation:

$$T_i = \sqrt{t_{x,i}^2 + t_{y,i}^2 + t_{z,i}^2}, \; i \in 1:N \hspace{1cm} \text{Equation 1B}$$

where $T_i$ equals the corrected magnitude of acceleration and $t_{x,i}$, $t_{y,i}$ and $t_{z,i}$ representing the x, y and z components of acceleration respectively. Hence, the raw accelerometer data for each limb and for each axis is converted into a translated smoother absolute value as defined by equations above.

Block 103 represents pre-processing of the cleaned/smoothed values to achieve feature extraction and annotation. The key purpose of feature extraction is to calculate features which are required for modeling the movement captured by the accelerometer and represented by the accelerometer data. The following features may be calculated from the smoothed magnitude data from each limb of the infant movement on a sample-by-sample basis:

$$T_{1,i} = \max(T_{left\text{-}arm,i}, T_{right\text{-}arm,i})$$

$$T_{2,i} = \min(T_{left\text{-}leg,i}, T_{right\text{-}leg,i}) \hspace{1cm} \text{Equation 2A}$$

Maximum/minimum values of individual limbs $$\max(T_{1,i}, T_{2,i})$$

$$\min(T_{1,i}, T_{2,i}) \hspace{2cm} \text{Equation 2B}$$

Overall maximum/minimum for all limbs $$T_{1,i} = T_{left\text{-}arm,i} * T_{right\text{-}arm,i}$$

$$T_{2,i} = T_{left\text{-}leg,i} * T_{right\text{-}leg,i} \hspace{1cm} \text{Equation 2C}$$

Power product of individual limbs $$T_i = T_{1,i} * T_{2,i} \hspace{2cm} \text{Equation 2D}$$

Overall power product of individual limbs $$\text{Correl}(T_{left\text{-}Limb,i}, T_{right\text{-}Limb,i}) \hspace{1cm} \text{Equation 2E}$$

Correlation between left and right limb

A second set of features is created from temporally aggregating information from the samples. For each data point, a new set of features is added to that point based on a temporal aggregation of neighboring data values. For each of the sample-based features, the maximum, minimum, mean, standard deviation, and z-value of all neighboring samples in a time window of ±0.5-seconds, ±1-second and ±2-seconds is calculated.

After smoothing, calculating and aggregating features, the accelerometer data is represented in terms of features extracted from the data. The feature vector combination for this modeling consists of a total of one-hundred and sixty-six (166) features classified as either "sample features," "temporal features" or "correlation features." There are ten (10) sample features consisting of smoothed magnitude of each of the limbs (i.e., LA, RA, LL, RL), product power of limbs, overall power of the limbs, maximum values for limbs and overall maximum of the limbs. The one-hundred and fifty (150) temporal features are derived from the ten (10) sample based features with five (5) functions applied over three (3) temporal windows. The five (5) functions are maximum, minimum, mean, standard deviation and z-value. There are also six correlation features for the correlation of the arms (RA with LA) and legs (LL with RL) over three (3) temporal windows.

At this point, the processed data can be evaluated by comparison to a reference standard in order to determine whether a subject whose extremity movements have been evaluated is at risk of a neurological or other condition. Preferably, the standard is based at least in part on the maximum acceleration magnitude of one or more of a subject's limbs. When the maximum acceleration magnitude is measured across a 2 second window, the resulting data, when compared with a reference standard, is indicative of whether a subject is at heightened risk of developing cerebral palsy.

Another use of the processed data is to generate models or standards for use in the clinical evaluation of neurological conditions, for example. This is shown in FIG. 1 in block 104, which represents modeling (e.g., by Graphical Models Toolkit (GMTK)) of the sample, temporal and/or correlation features to create a reference standard. The features are used to train a statistical model in conjunction with a trained observers coding of videos which are then used as the reference standard. In one embodiment, the statistical model is generated using statistical analysis software (e.g., RANDOM FOREST), support vector machines (SVMs) and Naive Bayes. An SVM training algorithm builds a model that predicts whether a new example falls into one category or the other. The model can correlate to Prechtl's qualitative assessment of general movements. Under the Prechtl model, "general movements" (GMs) in normal infants are described as elegant, smooth, variable in sequence, intensity and speed with a clear beginning and end, while "cramped-synchronized general movements" (CSGMs) in abnormal infants are described as rigid limbs moving in near synchrony. CSGMs have high predictive value for the development of cerebral palsy. Once trained, the models are fixed and used to recognize movements of monitored infants in a clinical setting.

According to embodiments of the invention, the processed data from the monitored infant may be used to categorize the infant into a risk group, i.e., a high risk or a low risk group. For example, a monitored infant may be characterized as having the presence or absence of abnormal movements in the form of type, number, synchronicity, etc. In one embodiment, the software uses a combination of sample, temporal and correlation features from the data to create an algorithm to identify, e.g., abnormal movements such as those known as CSGMs. Abnormal movements identified may indicate that the infant has an increased risk for cerebral palsy, seizures, autism, mental retardation, intraventricular hemorrhage, cognitive delay or other neurological or motor conditions. The information may be used by the clinician to assign or assess a risk status of the infant.

The present system and methods can be used to predict neurological disorders in infants using a non-invasive measure based on spontaneous movements in infants. At least one advantage of the present system is that it substantially or completely overcomes the limitations associated with human observers, i.e., subjectivity and observer fatigue among other limitations. The present system can also permit accurate assessment of energy expenditure due to physical activity in babies. Additionally, many adult conditions, such as obesity and osteoporosis, are now known to have origins very early in life and of which correlate to infant movement, and the present system can be used as a predictive tool to assess risk of developing these conditions later in life.

EXAMPLES

Example 1

Data Collection and Analysis

Test Subjects and Protocol.

Ten (10) preterm infants at 30-43 weeks corrected gestational age were selected for the experiment. Five accelerometers were used for data collection. Devices were embedded in cloth bands that were placed around the wrists, ankles and forehead of the infants with a canonical anatomical orientation. Each accelerometer measured three (3) orthogonal axes of acceleration on the head and each of the four (4) limbs. All infants were monitored and videotaped for one hour in an isolette wearing only a diaper and with all swaddling removed. The ambient temperature of the isolette was adjusted and maintained to standard levels. A video camera having a mid-sagittal view of the infant was positioned above the isolette at a downward angle of 45 degrees to record motion for video scoring.

Data Collection and Analysis.

The accelerometers transmitted data that was sampled non-uniformly at approximately 19 Hz in real-time to a computer. The raw accelerometer data consisted of real valued samples of the three (3) axes measuring the degree of acceleration due to gravity and changes in limb motion. Although data was collected from four limbs and the forehead, subsequent analysis demonstrated that head movement did not substantially vary and was excluded from further analysis.

Data Annotation.

Figure 12A:
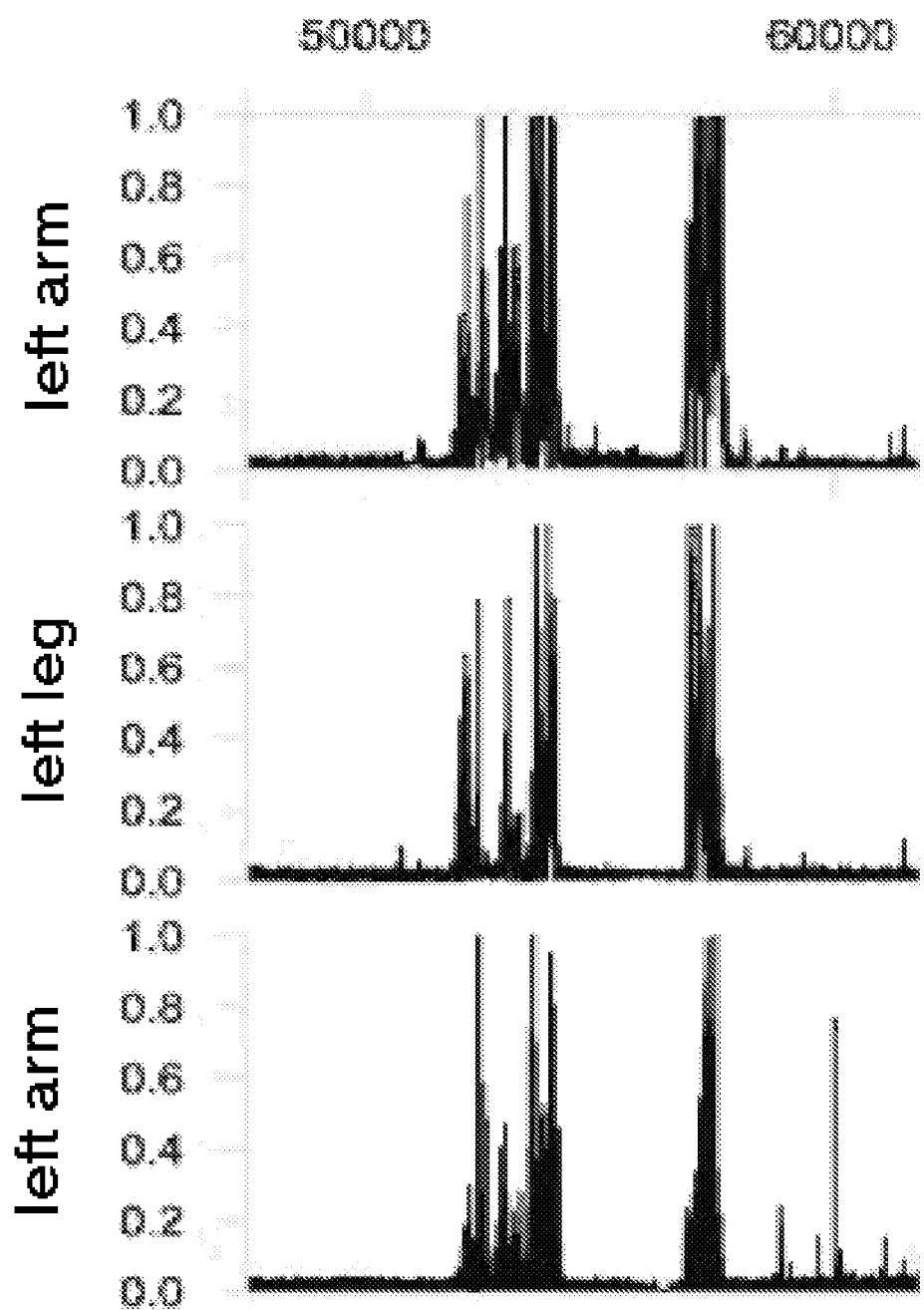
FIG. 12 shows accelerometer data for the four limbs of subjects along with the manual annotation of the visually observed data based on the Prechtl model for identifying CSGMs.
Figure 12B:
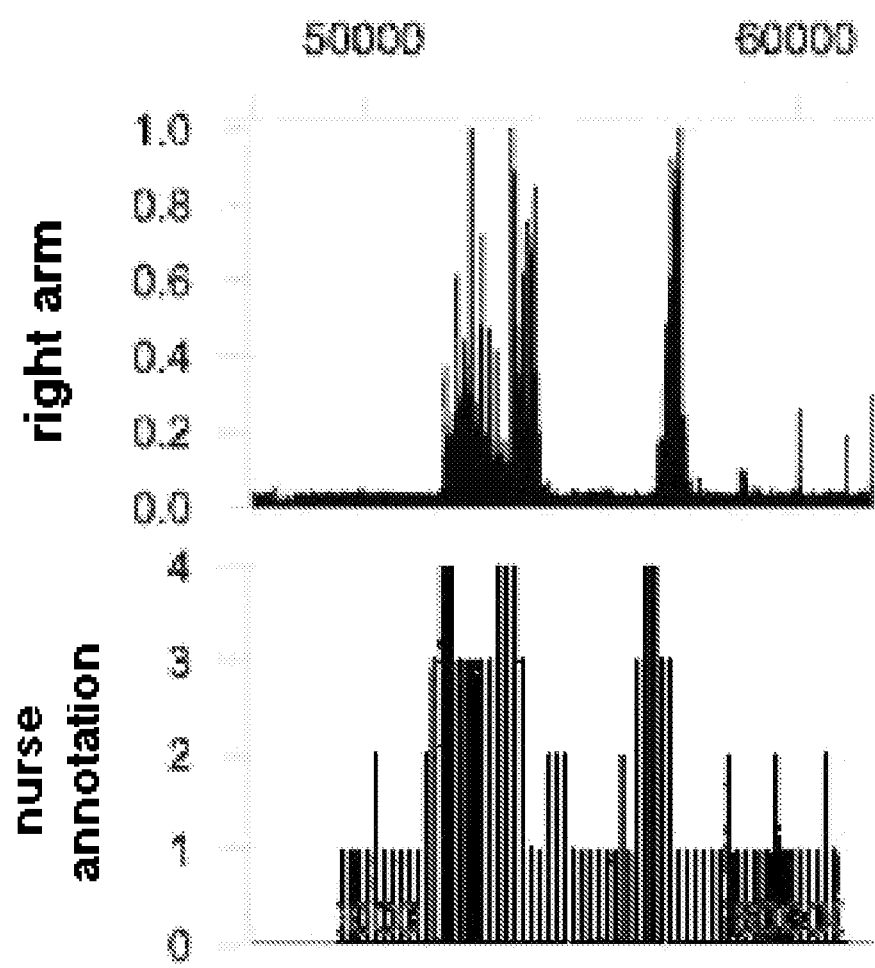

For comparison to the accelerometer data, the collected video data was manually annotated based on the Prechtl model for identifying CSGMs. A healthcare provider trained in the assessment identified windows of time in the video in which the infants demonstrated CSGMs. The healthcare provider annotated start and stop time for each CSGM observed. This scoring technique provided a label for every time sample, where the label was either "Movement Observed" or "Movement Not Observed". The annotated data was then synchronized with the corresponding timestamps in the video and accelerometer data (see FIG. 12).

Accelerometer Data Processing.

The raw accelerometer data was collected at 19 Hz and was indexed by a time stamp. Each time stamp had associated with twelve (12) real numbers corresponding to three (3) axes of acceleration data collected for each of four (4) limbs. This raw data required significant cleaning and processing to support effective modeling. The result of the data processing was to create one-hundred and sixty-six (166) values associated with each time stamp. These were "features" that could be correlated with video observations at the same time stamp and were the bases of the CSGM modeling.

There were three primary artifacts in raw data that were accounted for in preprocessing. The first was based on that the data was not collected at uniform intervals. Although each reading was accurately time-stamped, the sampling frequency was irregularly spaced with a 19 Hz average. This made calculating features based on frequency analysis outside the scope of this study. The second was that every triple of accelerometer readings contained a one (1) gram component due to gravity, which was indistinguishable from a one (1) gram change in movement in an infant. Based on the orientation of the infant's limbs, this component was distributed across the three (3) axes in different proportions at different times. The third was that there were periods of time in the collected data in which various NICU (personnel) medical interventions invalidated a few seconds of the data. The impact of these artifacts was reduced as follows.

By reviewing the video, periods of time were identified in which the accelerometer data was not generated by spontaneous movements in the infant. Examples of non-spontaneous movement periods included, e.g., pacifier adjustments by the NICU nurses, bumping of the isolette during temperature adjustments, and adjustments to the monitoring equipment. Removing this data resulted in gaps in the data stream that were conceptually similar to the already irregularly collected data samples although they were an order of magnitude larger. Each infant subsequently had a different absolute number of data points N that nonetheless spanned an hour.

To eliminate systematic biases in the readings that were not related to motion, such as gravity and accelerometer calibration drift, the resulting data was smoothed by translation relative to the mean of a ten (10) second window centered on each data point:

$$t'_{i,j} = t_{i,j} - m_{i,j} \; [i \in 1:N, j \in x,y,z] \qquad \text{Equation 1:}$$

Translation $$m_{i,j} = \text{mean}(t_{k,j}) \; [i-5 \; \text{sec}: k: i+5 \; \text{sec}]$$

For every sample time i and every axis j, the mean of a ten (10) second window centered at time i was subtracted from the observed data point $t_{i,j}$. The number of data points over which the mean was calculated was not constant because the data was collected at non-uniform intervals and because some data was removed due to intervention. However, the mean was calculated over the same duration of time. This step served to eliminate the effect of gravity and any other systematic constant offset in our readings (e.g., calibration drift) without reducing the number of data points.

Modeling pertained to changes in the motion of the limbs of the test subject infants. As a result, the three (3) axes from each accelerometer were merged into a single value that captured the overall magnitude of the smoothed data. For each time stamp, this resulted in four (4) new data values, one that aggregated the motion from each limb. These were the first four (4) features and represented the "corrected acceleration magnitude".

$$F_i^L = \sqrt{(t'_{i,x})^2 + (t'_{i,y})^2 + (t'_{i,z})^2}$$

$$i \in 1:N$$

$$L \in \{\text{left arm, right arm, left leg, right leg}\} \qquad \text{Equation 2:}$$

Corrected Acceleration Magnitude

This method of data preprocessing was invoked to ensure that the number of data points was not reduced so that they could be matched to the video annotations with high temporal fidelity.

Feature Extraction.

From the smoothed stream of accelerometer data, statistical features were extracted for analysis. The features chosen were based on CSGMs specifically and GMs broadly. The following instantaneous sample-based features for each data point were calculated.

Maximum values of the corrected acceleration magnitude of the upper and lower body:

$$F_i^5 = \max(F_i^{\text{left-arm}}, F_i^{\text{right-arm}})$$

$$F_i^6 = \max(F_i^{\text{left-leg}}, F_i^{\text{right-leg}})$$

Maximum of all the limbs:

$$F_i^7 = \max(F_i^{\text{left-arm}}, F_i^{\text{right-arm}}, F_i^{\text{left-leg}}, F_i^{\text{right-leg}})$$

Product of the corrected magnitude of the upper and lower body:

$$F_i^8 = F_i^{\text{left-arm}} * F_i^{\text{right-arm}}$$

$$F_i^9 = F_i^{\text{left-leg}} * F_i^{\text{right-leg}}$$

Product of the corrected magnitude of the total body:

$$F_i^{10} = F_i^{\text{left-arm}} * F_i^{\text{right-arm}} * F_i^{\text{left-leg}} * F_i^{\text{right-leg}}$$

Several features were calculated based on functions that aggregated over windows of time: the mean; the maximum; the minimum; the standard deviation; and the z-value. The time periods included one (1) second, two (2) seconds or four (4) seconds centered on the current data point. The data that we aggregated over included each of the first ten (10) features. This resulted in an additional one-hundred and fifty (150) features.

The final six (6) features that were calculated were the Pearson correlation between the left and right arm and the right and left leg. Although the correlation was for a single pair of data points, the same three time periods (1 second, 2 seconds or 4 seconds) as above as above to calculate the aggregate statistics required for each Pearson correlation calculation.

$$F_i^{\{161,162,163\}} = \text{Correl}_{\{1s,2s,4s\}}(F_i^{\text{left-arm}}, F_i^{\text{right-arm}})$$

$$F_i^{\{164,165,166\}} = \text{Correl}_{\{1s,2s,4s\}}(F_i^{\text{left-leg}}, F_i^{\text{right-leg}})$$

Modeling Prechtl Cramped-Synchronized General Movements.

The target data that was modeled were taken from the start and stop times that the trained healthcare provider marked when observing CSGMs. The feature vector for each data point consisted of a total of one-hundred and sixty-six (166) features derived from both instantaneous data and temporal features as described above. The healthcare provider's annotations provided a binary target class for each feature vector that was the value that we were trying to model and predict.

To predict a class, RANDOM FORESTS was utilized. As known by one of ordinary skill in the art, RANDOM FORESTS builds several "trees" based on a random subset of available features. Each tree is trained on a different bootstrap sample of the training data. During testing, each decision tree in the forest is presented with a single feature vector (with an unknown class) and votes on a classification. The final classification is based on the votes from all the trees in the "forest." Feature choices were additionally validated using support vector machines (SVMs) in a different software environment.

Results.

Figure 3:
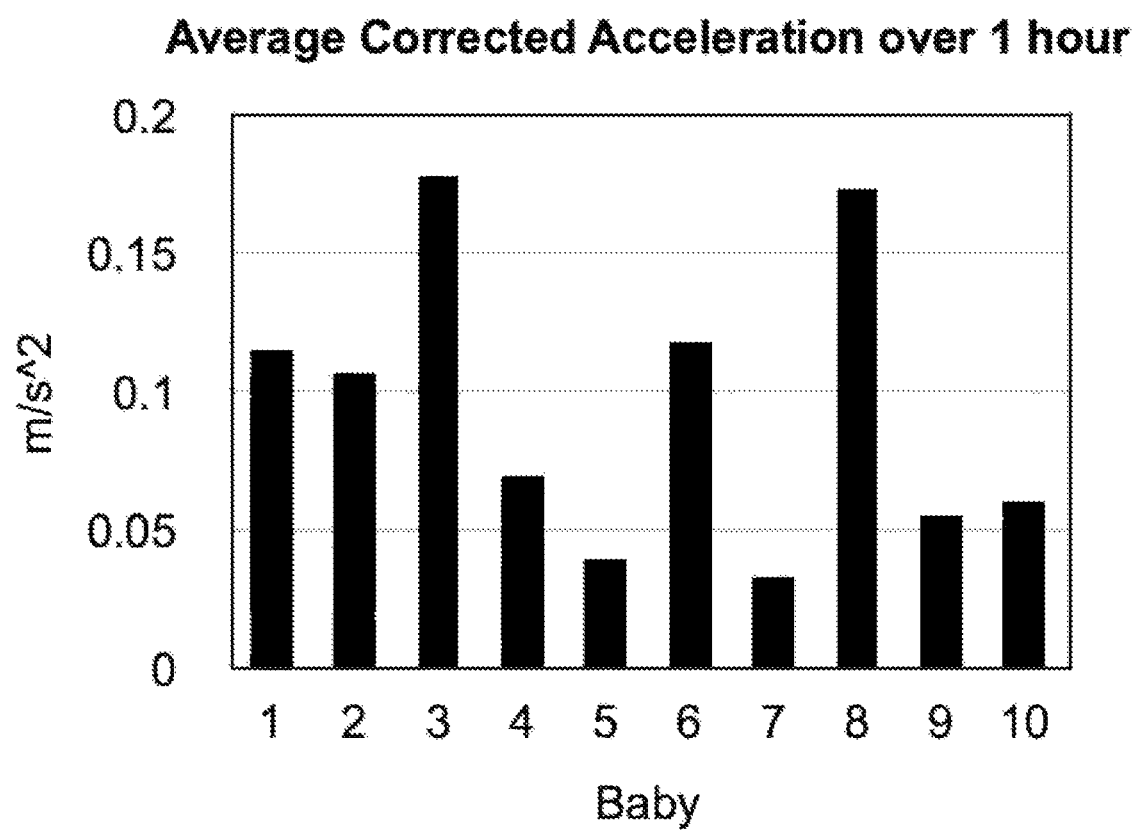
FIG. 3 is a graph showing the average corrected acceleration for each infant over the entire one (1) hour observation period (average across all times of the average of four limbs at each time sample).
Figure 4:
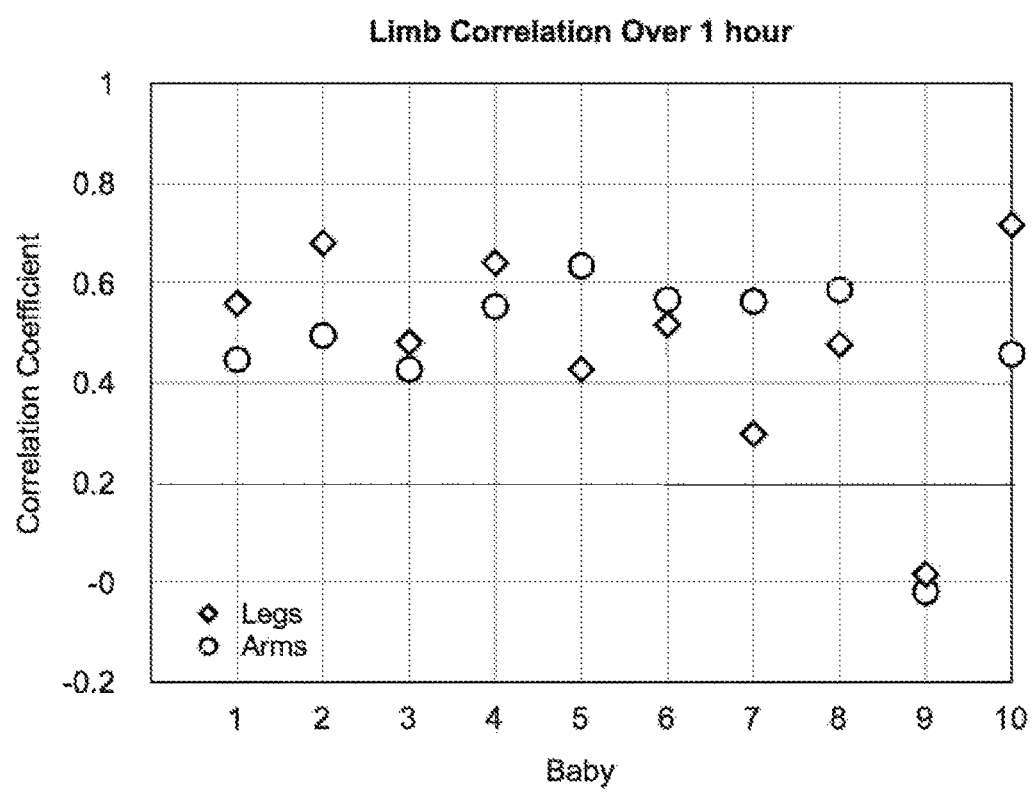
FIG. 4 is a graph showing the Pearson correlation calculated between the arms and between the legs of each infant.
Figure 5:
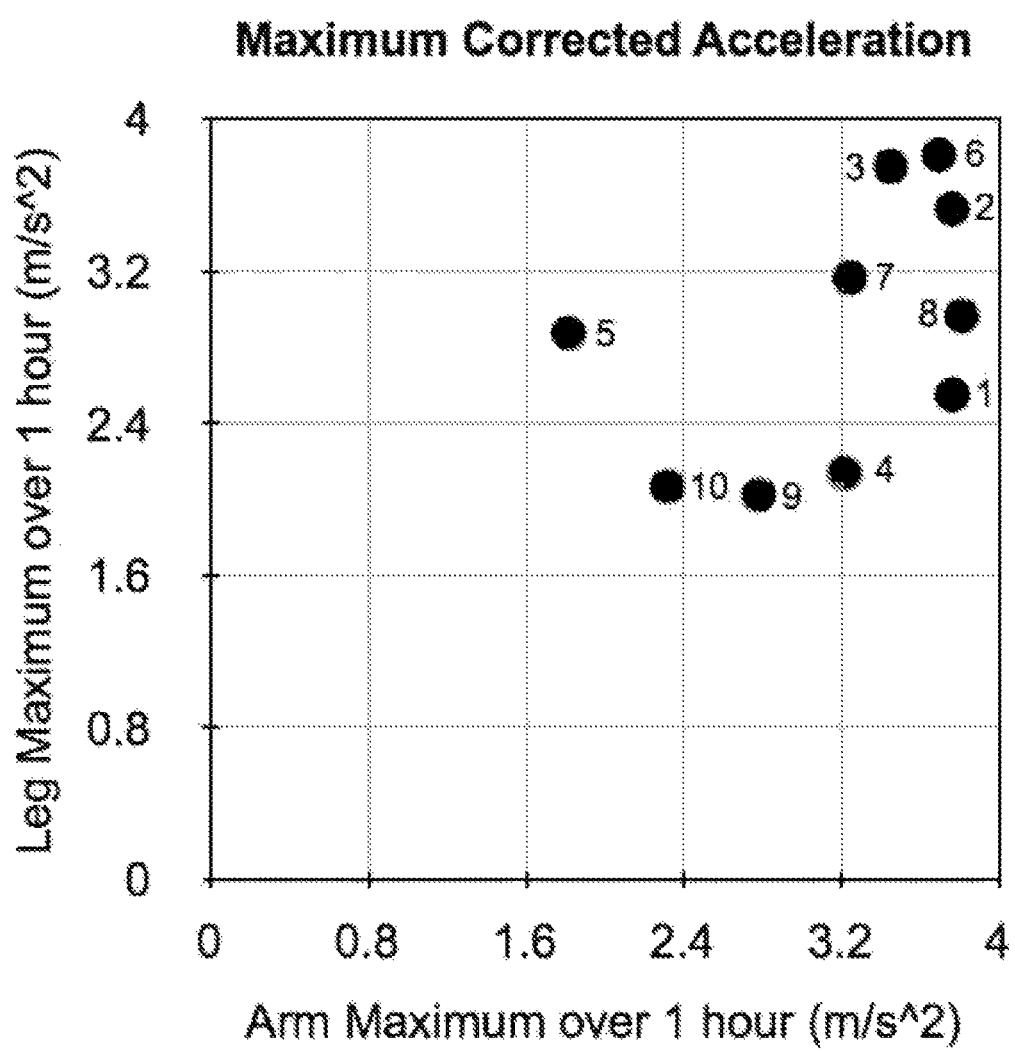
FIG. 5 is a graph showing a scatter plot of the maximum corrected arm and leg acceleration observed and the average corrected acceleration observed.
Figure 6:
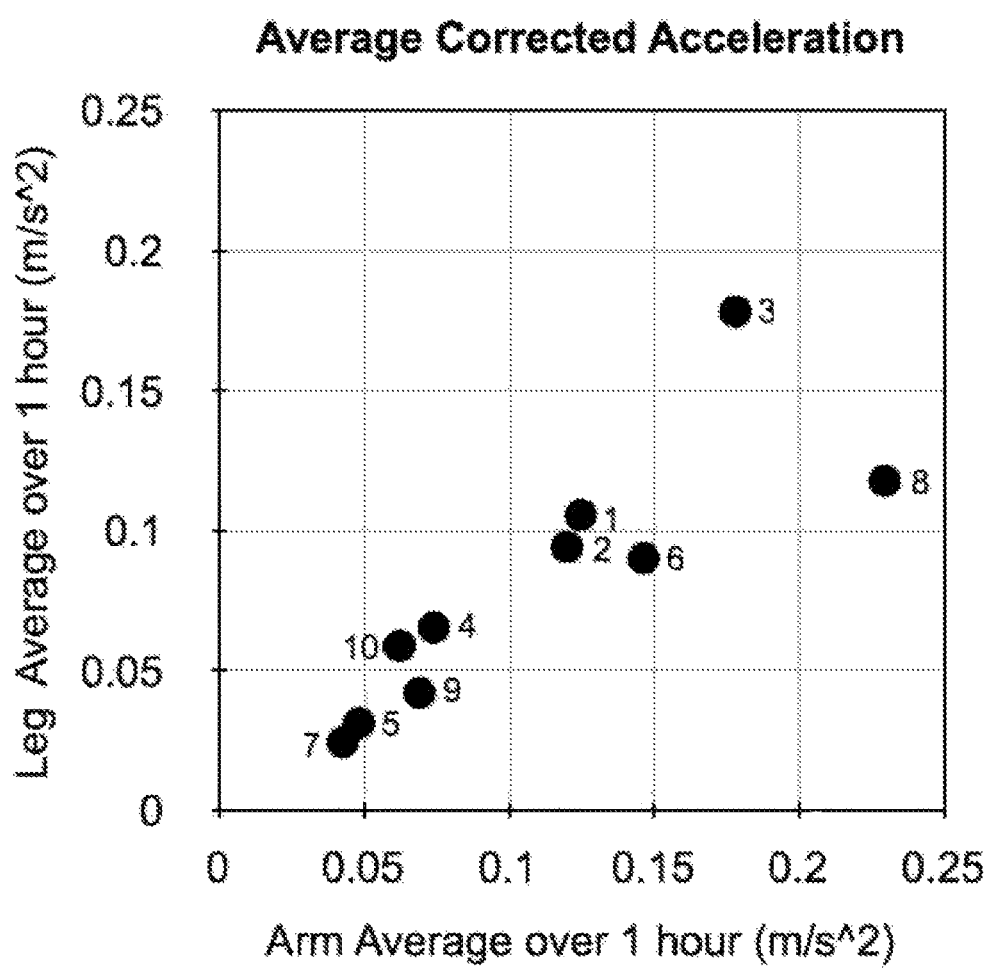
FIG. 6 is a graph showing a scatter plot of the average corrected arm and leg acceleration.

The average overall corrected acceleration magnitude for all infants was 0.095 m/s², with an average corrected arm acceleration of 0.11 m/s² and average corrected leg acceleration of 0.08 m/s². The maximum arm acceleration noted in any infant was 3.80 m/s² and the maximum leg acceleration was 3.87 m/s². FIG. 3 shows the average corrected acceleration for each infant over the entire one (1) hour observation period (average across all times of the average of four limbs at each time sample). A wide range of average accelerations reflected wide variability in limb motion. FIG. 4 shows the Pearson correlation calculated between the arms and between the legs of each infant. The right arm and left arm had an average correlation coefficient of 0.47, with one (1) being perfectly correlated and zero (0) being no correlation. The right leg and left leg had an average correlation coefficient of 0.48. FIGS. 5-6 show a scatter plot of the arm and leg acceleration observed and the average corrected acceleration observed. A strong correlation is seen between arm and leg acceleration.

Figure 7:
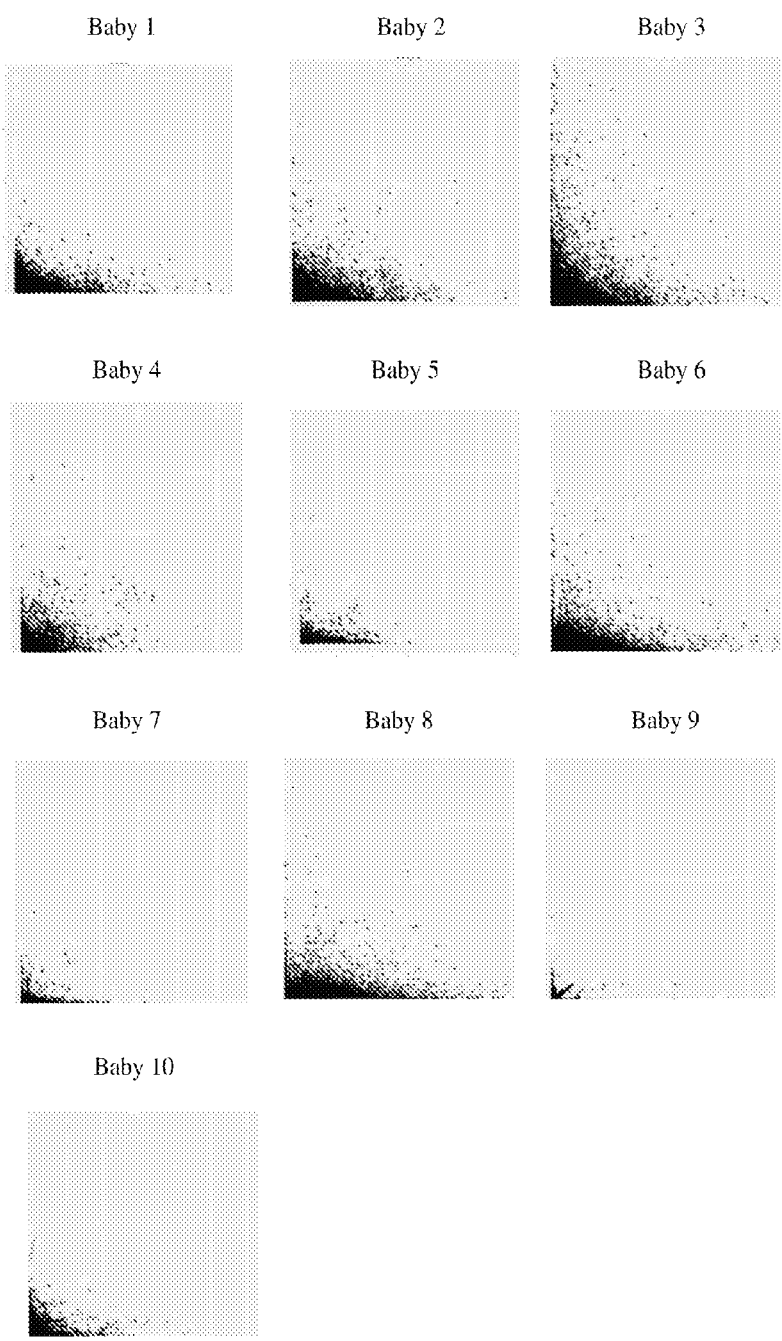
FIG. 7 is collection of scatter plots showing the corrected acceleration magnitudes of arms versus legs of subjects.

FIG. 7 is scatter plot of the product of corrected arms versus corrected legs. The x-axis of each graph is the product of the corrected acceleration magnitude of the left and right arm. The y-axis of each graph is the product of the corrected acceleration magnitude of the left and right leg. This graph reflects both the quantity and variability of the motion and also reflects symmetry of motion. Symmetric upper body motion would plot high on the x-axis, symmetric lower body motion would plot high on the y-axis and whole body motion would plot high on the line y equals x.

The healthcare provider identified 102 total CSGMs in six of the ten infants in the study. Each infant generated approximately 70,000 data points for a total of approximately 700,000 samples in our data. Using 10-fold cross-validation we applied the RANDOM FOREST algorithm to the data. The algorithm was trained on 70% of the data points and then tested on 30% of the data points. The algorithm achieved an average sensitivity of 99.2% and an average specificity of 99.6% to recognize CSGMs identified by the healthcare provider at any given time point. RANDOM FOREST results were compared analysis by a separate support vector machine (SVM) machine learning algorithm providing independent validity of software implementation correctness. FIG. 8 is a table of patient gestational age (GA). FIG. 9 is a table of Temporal Feature Calculation Components. FIG. 10 is a table of Modeling Results.

In order to validate our experimental setup and the accelerometers' ability to perform movement assessments, we first conducted an analysis in which a nurse scored the videos for periods of infant activity. Using the 4-point Giganti scale [20] we had a nurse annotate the video data at 110 time points throughout the hour of data. 50 annotations were made at the top of every minute for 50 minutes and 60 annotations were made every ten seconds for the remaining 10 minutes. Visual and statistical analysis demonstrated high correlation between the nurse's labels and the raw data. A portion of the data is shown in FIG. 2. 10 minutes of data from the 4 limbs are shown in the top 4 graphs black with the nurse's scoring in red in the bottom graph.

The average overall corrected acceleration magnitude for all infants was 0.095 m/s$^2$, with an average corrected arm acceleration of 0.11 m/s$^2$ and average corrected leg acceleration of 0.08 m/s$^2$. The maximum arm acceleration noted in any infant was 3.80 m/s$^2$ and the maximum leg acceleration was 3.87 m/s$^2$. FIG. 3 shows the average corrected acceleration for each baby over the entire 1-hour observation period (average across all times of the average of four limbs at each time sample). A wide range of average accelerations reflected wide variability in baby motion. FIG. 4 shows the Pearson correlation calculated between the arms and between the legs of each baby. The right arm and left arm had an average correlation coefficient of 0.47, with 1 being perfectly correlated and 0 being no correlation. The right leg and left leg had an average correlation coefficient of 0.48. FIGS. 5 and 6 show a scatter plot of the arm and leg acceleration observed and the average corrected acceleration observed. A strong correlation is seen between arm and leg acceleration.

The physical therapist identified 102 total CSGMs in six of the ten infants in the study. Each baby generated approximately 70,000 data points for a total of approximately 700,000 samples in our data. Using 10-fold cross-validation we applied the 3 algorithms to the data. Each technique produced different results that traded off sensitivity and specificity. Accuracies ranged from 70%-90%. achieved an average sensitivity of 99.2% and an average specificity of 99.6%. Detailed measurements are shown in Table 1 below.

TABLE 1

Modeling Results

| Baby ID | CSGM Present | Decision Tree | | SVM | | DBN + Random Forest | |
|---|---|---|---|---|---|---|---|
| | | Sensitivity | Specificity | Sensitivity | Specificity | Sensitivity | Specificity |
| 1 | No | — | 0.894 | — | * | — | 0.490 |
| 2 | Yes | .089 | 0.957 | 0.087 | 0.945 | 0.512 | 0.781 |
| 3 | No | — | 0.864 | — | * | — | 0.420 |
| 4 | Yes | 0.137 | 0.965 | 0.082 | 0.964 | 0.459 | 0.793 |
| 5 | Yes | 0.092 | 0.967 | 0.037 | 0.986 | 0.611 | 0.906 |
| 6 | Yes | 0.092 | 0.967 | 0.043 | 0.976 | 0.414 | 0.788 |
| 7 | Yes | 0.057 | 0.969 | 0.069 | 0.984 | 0.575 | 0.800 |
| 8 | Yes | 0.212 | 0.830 | 0.147 | 0.914 | 0.760 | 0.394 |
| 9 | No | — | 0.979 | — | * | — | 0.737 |
| 10 | No | — | 0.957 | — | * | — | 0.822 |
| Average | — | 0.103 | 0.939 | 0.069 | 0.964 | 0.498 | 0.764 |

Figure 11:
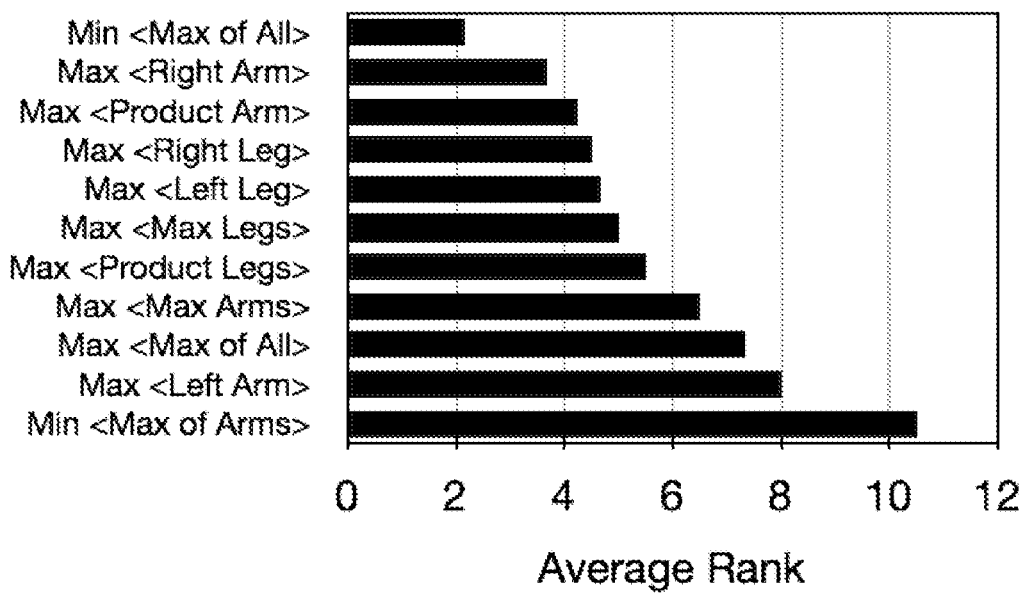
FIG. 11 is a chart showing the most informative features using an informational gain analysis.

Note:
Algorithmic limitations (*) and lack of true positives (—) prevented some entries from being calculated We conducted an analysis of the most informative features that were identified by the decision tree modeling. For each decision tree that was created in each of the ten cross validation folds we ranked the features according to their independent information gain to identify which single feature was the most correlated with CSGMs. For each feature we averaged the rank across the ten trees. FIG. 11 shows the result of the informative features.

The most informative feature was the minimum across a 2 second window of the maximum acceleration magnitude of all limbs for a given sample. This demonstrates that recognizing CSGMs requires observing a sustained motion. CSGMs are not particularly high-energy motions however, and this suggests that normal motions are do not sustain a continuously observed acceleration on all limbs for an entire 2 second window. The next nine most informative features were based on recognizing peak accelerations. This suggests that the sensor signature of CSGMs has sudden stops and starts although the movement itself is not characterized by a lot of high frequency motion.

Finally 2 of the top 4 features were correlated with the right side of the body. This is a curious result, but retrospective analysis of the cohorts medical records indicates that the majority of the patients had left side hemorrhaging that was apparently manifesting in right side motion.

The experiment resulted in a successful implementation of infant accelerometer monitoring for use in identifying CSGM's and therefore predicting risk of developing neurological based disorders manifested by abnormal motor movement. A successful model was created based on CSGMs using acceleration-only data with high accuracy, sensitivity and specificity. The results suggest a high correlation between the manual annotations of the healthcare provider based on the video and the accelerometer data. Since data was transmitted wirelessly in real-time, it is more suitable to clinical applications and potential real-time feedback. The presence of CSGM's indicates high risk for CP development and therefore the accelerometer system's identification of CSGM's in an infant classifies that infant into a high risk category.

Example 2

Wireless Accelerometer Design

An accelerometer produced for use with the present system consisted of (1) a microcontroller and radio board and (2) a sensor and power board. The microcontroller and radio board included a 2.4 GHz RF transceiver with an embedded 8051-compatible microcontroller, a chip antenna, a 32K EEPROM, and a 20-pin connector The 32 KB serial EEPROM is used to store the application program. The transceiver used a GFSK modulation scheme in the 2.4 GHz ISM band. It had 125 different frequency channels that are 1 MHz apart and supported frequency hopping among them. The maximum RF output power was 0 dBm at the maximum data rate of 1 Mbps. The output power, data rate, and other RF parameters were set from software. A chip antenna was used to radiate RF signals with a high-performance 2.4 GHz antenna measuring only 6.5 mm×2.2 mm×1.0 mm and its maximum gain was 0.8 dBi.

The power system of the accelerometer consisted of a lithium coin battery (CR1632), a step-up switching regulator, a load switch, and a power path switch. The battery was connected on the bottom side of the sensor and power board. The accelerometer used the CR1632 battery, whose nominal output voltage and capacity are 3V and 125 mAh, respectively. In order to supply stable power to the wireless accelerometer, a step-up switching regulator was used. This switching regulator generates a constant 3V regardless of the battery's actual output voltage.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure.

Recitation of value ranges herein is merely intended to serve as a shorthand method for referring individually to each separate value falling within the range. Unless otherwise indicated herein, each individual value is incorporated into the specification as if it were individually recited herein. All references cited herein are incorporated by reference in their entirety.

What is claimed is:

1. A system for determining an infant's risk for experiencing a medical disorder, comprising:
    one or more wireless accelerometers for attachment to one or more extremities of an infant subject, each accelerometer configured to measure physical movement from one of the subject's extremities;
    a base station in wireless communication with the accelerometers; and
    a processing circuit electrically coupled to the base station, the processing circuit being adapted to measure a maximum acceleration magnitude of the subject's extremities over a period of 2 seconds, perform statistical analyses of data from the accelerometers, and compare the processed data to a reference standard in order to determine whether the subject is at risk of experiencing the medical disorder.

2. The system of claim 1, wherein the medical disorder is selected from the group consisting of a neurological disorder and a motor skills disorder.

3. The system of claim 1, wherein the medical disorder is selected from the group consisting of cerebral palsy, mental retardation, autism and intraventricular hemorrhage.

4. The system of claim 1, wherein the one or more extremities are selected from the group consisting of a right arm, a left arm, a right leg, and a left leg.

5. The system of claim 1, wherein the processing circuit utilizes a statistical machine learning technique selected from the group consisting of Naive Bayes, Support Vector Machines, and a pruned Decision Tree.

6. The system of claim 1, wherein the wireless accelerometer weighs less than 5 grams.

7. The system of claim 1, wherein the wireless accelerometer has a surface area of 1 $cm^2$ or less.

8. The system of claim 1, wherein the processing circuit is adapted to measure the maximum acceleration magnitude for all the extremities of the subject.

9. A method for diagnosing whether an infant subject is at risk for a predetermined medical condition, comprising:
    measuring movements from a plurality of limbs of the subject, wherein the measuring is performed by a plurality of wireless accelerometers attached to the plurality of limbs, the plurality of accelerometers providing data wirelessly to a base station;
    normalizing the data;
    calculating one or more features using the normalized data, wherein the one or more features include a maximum acceleration magnitude of the limbs of the subject over a predetermined period of time, the maximum acceleration magnitude being measured over a period of 2 seconds; and
    comparing the features to a standard to determine whether the subject demonstrates certain predetermined movements which indicate that the subject is at risk for the medical condition.

10. The method of claim 9, wherein the subject is a premature infant.

11. The method of claim 9, wherein the comparing step utilizes a statistical machine learning technique selected from the group consisting of Naive Bayes, Support Vector Machines and a pruned Decision Tree.

12. The method of claim 9, wherein the presence of the predetermined movements indicates that the subject is at risk for a neurological or motor skills impairment.

13. The method of claim 9, wherein the medical condition is selected from the group consisting of cerebral palsy, mental retardation, autism and intraventricular hemorrhage.

14. The method of claim 9, wherein the predetermined movements comprise Cramped-Synchronized General Movements.

15. The method of claim 9, wherein the maximum acceleration magnitude is measured for all the limbs of the subject.

* * * * *